US009827214B2

(12) United States Patent
Scheffler

(10) Patent No.: US 9,827,214 B2
(45) Date of Patent: *Nov. 28, 2017

(54) USE OF AN OLEOGEL CONTAINING TRITERPENE FOR HEALING WOUNDS

(71) Applicant: AMRYT RESEARCH LIMITED, Dublin (IE)

(72) Inventor: Armin Scheffler, Niefern-Öschelbronn (DE)

(73) Assignee: AMRYT RESEARCH LIMITED, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 15/142,679

(22) Filed: Apr. 29, 2016

(65) Prior Publication Data

US 2016/0317481 A1    Nov. 3, 2016

Related U.S. Application Data

(63) Continuation of application No. 13/509,416, filed as application No. PCT/EP2010/068157 on Nov. 24, 2010, now Pat. No. 9,352,041.

(30) Foreign Application Priority Data

Nov. 24, 2009   (DE) ................. 10 2009 047 092

(51) Int. Cl.

| A61K 9/10 | (2006.01) |
|---|---|
| A61K 47/46 | (2006.01) |
| A61K 31/047 | (2006.01) |
| A61K 31/19 | (2006.01) |
| A61K 9/00 | (2006.01) |
| A61K 9/06 | (2006.01) |
| A61K 31/56 | (2006.01) |
| A61K 47/06 | (2006.01) |
| A61K 47/44 | (2017.01) |
| A61K 31/045 | (2006.01) |

(52) U.S. Cl.
CPC ............ *A61K 31/19* (2013.01); *A61K 9/0014* (2013.01); *A61K 9/06* (2013.01); *A61K 31/045* (2013.01); *A61K 31/56* (2013.01); *A61K 47/06* (2013.01); *A61K 47/44* (2013.01)

(58) Field of Classification Search
CPC ........ A61K 9/0014; A61K 9/06; A61K 31/19; A61K 31/56; A61K 47/06; A61K 47/44
See application file for complete search history.

(56) References Cited

U.S. PATENT DOCUMENTS

| 4,142,224 A | 2/1979 | Wilson |
| 5,750,578 A | 5/1998 | Carlson et al. |
| 6,022,890 A * | 2/2000 | Bao ........ C07D 303/48 514/475 |
| 7,482,383 B2 | 1/2009 | Scheffler |
| 8,536,380 B2 | 9/2013 | Scheffler |
| 8,828,444 B2 | 9/2014 | Scheffler |
| 9,352,041 B2 * | 5/2016 | Scheffler .............. A61K 9/0014 |
| 2003/0087789 A1 | 5/2003 | Scheffler |
| 2005/0019426 A1 | 1/2005 | Wirth |
| 2007/0299285 A1 | 12/2007 | Scheffler |

FOREIGN PATENT DOCUMENTS

| CN | 1972668 | 5/2007 |
|---|---|---|
| DE | 103 17 400 | 11/2004 |
| DE | 103 29 955 | 2/2005 |
| DE | 10 2004 030 044 | 1/2006 |
| IL | 180057 | 11/2013 |
| JP | 61-205204 | 12/1986 |
| JP | 09-235293 | 9/1997 |
| JP | 2004-519411 | 7/2004 |
| JP | 2008-503530 | 2/2008 |
| JP | 2009-506981 | 2/2009 |
| KR | 10-2007-0046821 | 5/2007 |
| WO | WO 01/19365 | 3/2001 |
| WO | WO 01/72315 | 10/2001 |
| WO | WO 2004/016336 | 2/2004 |
| WO | WO 2005/123037 | 12/2005 |
| WO | WO 2006/135493 | 12/2006 |
| WO | WO 2008/046541 | 4/2008 |
| WO | WO 2009/090394 | 7/2009 |

OTHER PUBLICATIONS

Atherton et al, Great Ormond Street Hospital for Children, Epidermolysis Bullosa: An outline for professionals). Nov. 2003.*
Jaeger, et al., "Pharmakologie ausgewahlter Terpene", In: Pharmazeutische Zeitung, 2006, vol. 151, S. 16-25. (discussed in German Office Action dated Sep. 10, 2010).
Lasczyk, Melanie, "Triterpentrockenextrakt aus Birkenkork (Betula alba cortex)", Dissertation, Universitat Freiburg 1.Br., 2007. (discussed in German Office Action dated Sep. 10, 2010).
Maquart, Francois-Xavier, et al., "Stimulation of Collagen Synthesis in Fibroblast Cultures by a Triterpene Extracted From Centella Asiatica", Connective Tissue Research: An Internat. Healthcare, US, Bd. 24, Jan. 1, 1990, vol. 24, pp. 107-120, XP000946035, ISSN: 0300-8207, DOI: 10.3109/03008209009152427.
Shrikhande B.K., et al., "Development and Evaluation of Antiinflammatory Oleogels of *Bosewellia serrate* (GUGUL) and *Curcuma longa* (TURMERIC)", Indian Drugs, Indian Drug Manufacturers Association, In, Bd. 38, Nr. 12, Dec. 1, 2001, pp. 613-616, XP008005371, ISSN: 0019-462X.
Harish, B.G., et al., "Wound Healing activity and docking of glycogen-synthase-kinase-3-b-protein with isolated triterpenoid Lupeol in rats", In: Phytomedicine, 2008, vol. 15, S. 763-767.

\* cited by examiner

*Primary Examiner* — Mina Haghighatian
(74) *Attorney, Agent, or Firm* — Cooley LLP

(57) ABSTRACT

An oleogel comprising a non-polar liquid and a powder containing triterpene is provided as an oleogel that may be used for healing wounds.

18 Claims, 1 Drawing Sheet

USE OF AN OLEOGEL CONTAINING TRITERPENE FOR HEALING WOUNDS

CROSS-REFERENCE TO RELATED APPLICATIONS

This application is a continuation of U.S. application Ser. No. 13/509,416, filed May 11, 2012, now issued as U.S. Pat. No. 9,352,041, which is a national stage application of International Application No. PCT/EP2010/068157, filed Nov. 24, 2010, the entire content of each of which is incorporated herein by reference in its entirety.

TECHNICAL FIELD

The invention relates to the use of a triterpene-containing oleogel.

BACKGROUND OF THE INVENTION

Gels are finely dispersed systems made of a liquid phase and a solid phase, the solid phase forming a coherent three-dimensional framework and the two phases completely permeating one another. One essentially differentiates between hydrophilic gels and hydrophobic gels. The latter are also referred to as oleogels. Oleogels are based on a nonpolar liquid, for example, an oil, a wax, or a paraffin, to which a gel-forming agent is added to achieve the desired physical properties.

Such oleogels may be used for greatly varying purposes depending on the composition.

In particular in the pharmaceutical field, oleogels are used for topical applications. In these pharmaceutical oleogels, a gel-forming agent is provided in the gel in addition to the pharmaceutically active substances. A frequently used gel-forming agent for pharmaceutical oleogels is highly dispersed silicon dioxide, which is available under the trade name Aerosil®. Oleogels have pronounced thixotropy, i.e., they liquefy in the event of mechanical action and subsequently resolidify. Other gels, for example, gels having pectin as the gel-forming agent, cross-link under the effect of acid, and still others gel as a function of the temperature, for example, gelatins.

The use of a highly dispersed triterpene as an oleogel-forming agent and an oleogel having a highly dispersed triterpene as an oleogel-forming agent are described in DE 10 2004 030 044 A1.

Known substances for healing wounds, i.e., for healing skin wounds in humans and in mammals are, for example, dexpanthenol or chamomile extracts. In order to process these substances into applicable medications, however, auxiliary materials, such as emulsifiers, solvents, or preservatives are required. These auxiliary materials may have an interfering effect on the healing of wounds, however, and may additionally result in allergic reactions in some patients.

SUMMARY OF THE INVENTION

The object of the invention is to provide an effective preparation, which is simple to produce, for healing wounds of the skin, in particular for healing chronic wounds, which is additionally well tolerated with respect to allergies.

This object is achieved by a use as recited in claim 1. Embodiments and refinements are the subject matter of the subclaims.

According to the invention, an oleogel is used for healing wounds of the skin, which contains a nonpolar liquid and at least one triterpene-containing powder as an oleogel-forming agent, or such an oleogel is used to manufacture a medication for healing wounds.

Such an oleogel is fundamentally suitable for healing all types of wounds, for example, for healing wounds which are induced by external influences, such as accidents, and also for healing wounds, in particular chronic wounds, which are caused by skin diseases. Such a skin disease is, for example, the genetically related skin disease epidermolysis bullosa (EB). In humans who suffer from this disease, the mechanical connection between the various skin layers is inadequately formed, so that blisters and wounds may arise solely due to slight mechanical stresses.

Triterpenes, such as betulin, lupeol, betulinic acid, oleanolic acid, and similar compounds, are renewable raw materials which occur in comparatively high concentrations in birch bark, but which also occur in other plants or plant components, e.g., in rosemary leaves, mistletoes, or apple peels. Betulin, betulinic acid, lupeol, and oleanolic acid are pentacyclic triterpenes, of which the three first mentioned have a lupane framework and of which the oleanolic acid has an oleanene framework. The characteristic feature of the lupane group is a ring having five carbon atoms within the pentacyclic system, which has a α-isopentenyl group at the position C-19.

An arbitrary triterpene or an arbitrary triterpene composition, which is provided in powder form and is sufficiently finely pulverized to act as an oleogel-forming agent, is suitable as the oleogel-forming agent in the oleogel. A triterpene composition includes two or more different triterpenes. According to one example, the mean particle size of the at least one triterpene in the oleogel-forming agent is preferably between 20 nm and 50 μm, particularly preferably less than 10 μm.

In addition, a homogeneous particle size distribution is advantageously provided, which is to be understood hereafter to mean that a fraction of secondary agglomerates in the highly dispersed triterpene-containing powder is less than 20 weight-percent.

The present oleogel-forming agent, which is provided in the form of a micronized triterpene-containing powder, may also include, in addition to triterpenes, for example, betulin, betulinic acid, lupeol, or allobetulin, a fraction of other materials, for example, those materials which may also be naturally present in a specific fraction in triterpene-containing plant components, for example, birch bark, from which triterpenes may be extracted. The triterpene fraction in the oleogel-forming agent according to the invention is preferably greater than 80 weight-percent, particularly preferably greater than 90 weight-percent in relation to the weight of the oleogel-forming agent. The betulin fraction in relation to the triterpene fraction is advantageously greater than 60 weight-percent, and in particular greater than 80 weight-percent.

The at least one triterpene used as the oleogel-forming agent may be extracted with the aid of typical noncontinuous extraction methods (batch methods) or with the aid of typical continuous methods from plants or plant components, for example, from birch bark, rosemary, mistletoes, or apple peels, so that further statements in this regard may be dispensed with. Continuous methods for obtaining triterpenes from plant components, in particular betulin from birch bark, are described, for example, in WO 2001/72315 A1 or WO 2004/016336 A1.

If the at least one triterpene-containing powder is not provided after the extraction with the dispersibility, mean particle size, and homogeneous particle size distribution necessary for the gel forming properties, the powder may be subjected to various methods in order to achieve the desired particle size, homogeneity, and dispersibility. Various methods are known for this purpose: If the particle size in the powder is excessively high, collision or gravitation methods are suitable for pulverizing the particles. In addition, the possibility exists of dissolving the powder in a suitable solvent, for example, tetrahydrofuran (THF), and subsequently recrystallizing it. This crystallization may be performed, for example, by spray drying or cooling of a saturated solvent. The particle size may be set via the crystallization conditions. The crystallization conditions are dependent in the case of spray drying, for example, on the diameter of a nozzle via which the triterpene-solvent mixture is sprayed, and the temperature and the pressure in a chamber into which the mixture is sprayed. In the case of crystallization by cooling of a saturated solution, the crystallization conditions are dependent on the temperature gradients with respect to time during the cooling and the triterpene concentration in the solution. Finally, the possibility also exists of classifying an existing powder, in order to obtain a powder having a desired size distribution.

In some embodiments, the oleogel comprises a nonpolar liquid fraction. In further embodiments, the nonpolar liquid fraction comprises between 80 weight-percent and 99 weight-percent in relation to the total weight of the oleogel, and the triterprene fraction comprises between 1 weight-percent and 20 weight-percent in relation to the total weight of the oleogel.

The fraction of the nonpolar liquid in the oleogel is preferably between 88 weight-percent and 94 weight-percent and the fraction of the triterpene-containing powder is preferably between 6 weight-percent and 12 weight-percent.

Arbitrary nonpolar liquids, for example, plant, animal, or synthetic oils, waxes, and paraffins are suitable as the nonpolar liquid for the oleogel. The nonpolar liquid is, for example, a vegetable oil which is selected from one of the following: sunflower oil, olive oil, avocado oil, almond oil.

The advantage of this semisolid preparation in the form of an oleogel is in the simplicity of its formulation, the triterpene functioning simultaneously as a pharmaceutically active wound healing substance and as a gel-forming agent, so that additional gel-forming agents may be dispensed with. The oleogel is thus suitable in particular as a wound healing agent for allergy-prone skin.

Of course, however, the possibility also exists of adding other pharmaceutically active substances in pharmacologically active concentrations, such as dexpanthenol or chamomile extracts, to the oleogel, in addition to the triterpene present in the gel-forming agent. The oleogel having the nonpolar liquid and the triterpene-containing powder as the oleogel-forming agent represents an ideal foundation for such materials, because it may absorb lipophilic substances. The possibility thus also exists of already adding a lipophilic pharmaceutically active substance to the nonpolar liquid even before the oleogel is manufactured by adding the triterpene-containing powder.

In addition, an aqueous extract may be processed with the aid of the oleogel to form a stable emulsion.

BRIEF DESCRIPTION OF THE DRAWINGS

The invention is explained hereafter on the basis of examples, in particular with reference to the appended figures.

DETAILED DESCRIPTION OF VARIOUS EMBODIMENTS

Figure 1:
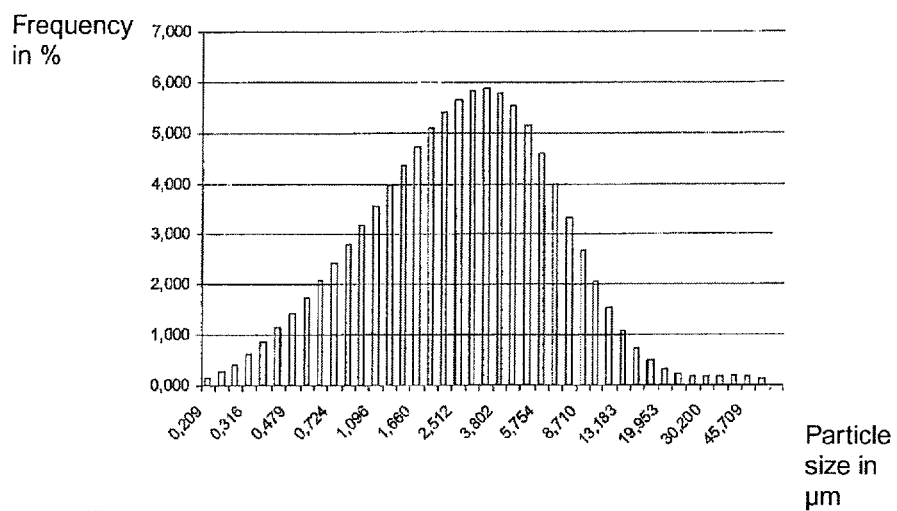
FIG. 1 illustrates the particle size distribution of an example of a highly dispersed oleogel-forming agent in an oleogel suitable for healing wounds.

FIG. 1 illustrates the particle size distribution of an example of a highly dispersed oleogel-forming agent in an oleogel suitable for healing wounds. In the example, the particle size is between 0.5 µm and 40 µm; the maximum of the size distribution is between 8 µm and 10 µm. According to gas chromatographic analysis, this powder contains 85 weight-percent betulin, 5 weight-percent betulinic acid, 3% oleanolic acid, 0.7 weight-percent lupeol, and 6.3 weight-percent other triterpene derivatives.

Using this powder as the gel-forming agent, an oleogel was produced, in that the powder was mixed, at 10 weight-percent in relation to the total weight of the oleogel, with sunflower oil. The result was a stable semisolid gel having strongly pronounced thixotropy (oleogel S10). This gel is referred to hereafter as oleogel S10, "S10" indicating a fraction of 10% of the triterpene-containing powder in the oleogel. Additional wound healing substances are not provided in oleogel S10.

An oleogel having a highly dispersed, triterpene-containing powder as the oleogel-forming agent is suitable as a wound healing agent for the treatment of arbitrary skin wounds of the human body. Such wounds may be wounds which are caused by accidents, e.g., cuts or abrasions or also burn wounds. However, such wounds may also be wounds which are intentionally required for therapeutic purposes, e.g., wounds after a split skin graft removal or wounds after a laser treatment, e.g., a laser treatment for removing tattoos or skin growths. An oleogel having a highly dispersed triterpene-containing powder as the oleogel-forming agent is also suitable as a wound healing agent for the treatment of wounds which are caused by skin diseases, e.g., epidermolysis bullosa.

FIRST EXAMPLE

The wound healing effect of a triterpene-containing oleogel (oleogel S10) was tested on the basis of the "porcine ex-vivo wound model," which is the subject matter of DE 103 17 400 B4. The epidermis and the upper part of the dermis were removed in a small circular area from skin samples of the pig ear having a diameter of 6 mm. In a first group of 10 samples, 10 µL of oleogel was introduced once for 48 hours into the wounds resulting in this way, in a second group of six samples, 10 µL Vaseline, which was used as a comparative preparation, was applied, and a third group of 10 samples remained untreated as the control group. After 48 hours, the skin samples were fixed and subsequently histologically studied.

Figure 2:
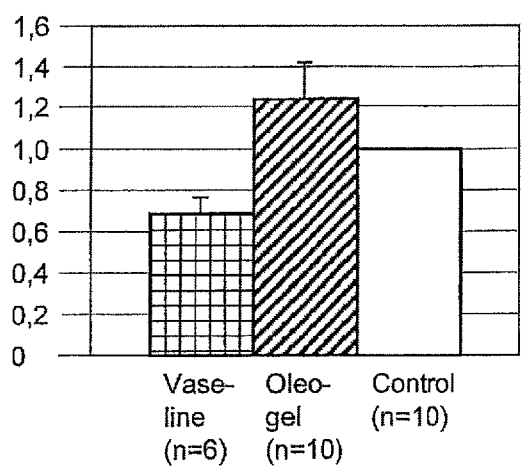
FIG. 2 illustrates the wound healing progress in the case of healing wounds according to the "porcine ex-vivo wound model" under the influence of a triterpene-containing oleogel.

The study showed, on the basis of the reepithelialization progress, improved wound healing in the samples treated using the oleogel in comparison to the other samples. The wound healing progress is graphically shown in FIG. 2 in the form of a bar graph. The left bar shows the wound healing progress for Vaseline, the right bar shows that of the control sample, and the middle bar shows that for the oleogel. As is apparent, the treatment using the oleogel results in a more rapid wound healing progress in comparison to both non-treatment and also to treatment using Vaseline.

In addition, the oleogel showed similarly good maintenance of the morphology of the wound edge as in the untreated samples. The number of the proliferative cells in the regenerating epidermis had a tendency to be reduced under the influence of the oleogel in comparison to the untreated sample, but was equal on the wound edge, while the Vaseline had statistically significantly fewer proliferative cells here.

SECOND EXAMPLE

Patient (f), 3 years of age diagnosis: epidermolysis bullosa junctionalis non-Herlitz
  wound status before treatment:
    flat, fibrinous coated chronic wound, right thorax
    no tendency to heal over more than four weeks
    size: 13.63 cm$^2$
  therapy until now:
    daily bandage change, wound care with Mepitel and Mepilex transfer; regular Octenisept skin disinfection.
  secondary diagnoses:
    MRSA colonization in six locations, no smear test from the treated location
    iron deficiency anemia
    alimentary dystrophy
    chronic pains
  beginning of therapy 15 July:
    daily oleogel S10 application, Mepilex transfer wound bandage
    concomitant therapy: antiseptic baths
    medication: ibuprofen 3×80 mg, Tavigil (2×5 mL)
  wound findings on 17 July:
    size: 9.58 cm$^2$ (approximately 30% decrease in wound area)
  flat uncoated wound
    epithelization on the wound edges and formation of an epithelial bridge

THIRD EXAMPLE

Patient (m), 4 years of age diagnosis: epidermolysis bullosa simplex
  initial findings:
    annular proliferating blisters and crusts
    back and both flanks
    present since five weeks
    massive itching
  therapy until now:
    Bepanthen, Fucidin, and Mepilex without sustained improvement
  beginning of therapy on 12 Dec. 2008:
    treatment using Octisept solution 2× daily oleogel S10; covering the wound with Mepilex transfer;
    medication: Fenistel drops; Aerius syrup; Excipial and Lipolotio two times daily; 5% Thesit in Unguentum leniens as needed during the day.
  Findings on 18 Dec. 2008:
    fewer blisters and crusts
    itching alleviated
  follow-up 2 May 2009 with continuation of the oleogel treatment;
  healing and absence of the itching

FOURTH EXAMPLE

Patient (f), 12 years of age diagnosis: recessive dystrophic epidermolysis bullosa
  wound status before therapy:
    left medial malleolus: flat, slightly inflamed, painful (visual analog scale 0-100: VAS 50), exuding (VAS 50) wound; present since 10 Apr. 2009
    right knee ventral: flat, slightly inflamed, slightly painful (VAS 15), exuding (VAS 40) wound; present since 13 Apr. 2009
  therapy until now:
    Urgotul; Mepilex lite
  therapy from 16 Apr. 2009;
    both wounds: Urgotul, Mepilex lite, daily bandage change
    left medial malleolus additionally with oleogel S10
  wound findings on 22 May 2009:
    both wounds healed
    left malleolus (oleogel S10): epithelized (VAS 100); slightly reddened (VAS 8); not painful or itching (VAS 0)
    right knee (control): epithelized with residual crust (VAS 90); slightly reddened (VAS 8), slightly painful (VAS 10), and itching (VAS 5)

FIFTH EXAMPLE

Patient (m), 57 years of age diagnosis: epidermolysis bullosa dystrophica inversa
  wound status before therapy on 18 Nov. 2008:
    flat fibrinous coated wounds
    size: 9.48 cm$^2$
    scrotal right and left,
    no healing over more than three months
  therapy until now:
    greatly varying ointments and creams, no improvement
  additional findings:
    wound colonization with staph. auereus, proteus
    diabetes mellitus, requires insulin
  beginning of therapy 18 Nov. 2008:
    oleogel S10: 2× daily
    wound dressing Mepilex transfer
  wound status on 24 Nov. 2008:
    almost completely healed, flat, fibrinous coated wound
    size: 0.65 cm$^2$
  follow-up:
    worsening after cessation of oleogel S10
  therapy attempt with Mirfulan cream, no significant improvement
    therapy attempt with Imlan Creme Pur, only slight improvement
    after renewed therapy with oleogel S10, healing The wound treatment using an oleogel, which includes a triterpene-containing powder as the oleogel-forming agent, already causes a usable healing process and a reduction in size of the wounds, and therefore significant abatement, after a few days. In the event of sustained treatment, the oleogel causes complete healing of the wound, in particular also the healing of chronic wounds in which no healing process had previously spontaneously begun. In the wound healing, the oleogel promotes the reepithelialization in particular and may thus be used in particular in the case of wound healing during the reepithelialization phase.

In addition to the outer epithelia mentioned in the examples, the oleogel is also suitable for healing of wounds on inner epithelia (mucosae), e.g., in the nose, stomach, or genital area. The oleogel may be administered orally harmlessly.

The triterpene composition (composition I) explained in connection with FIG. 1 is merely an example of a triterpene composition which has a wound healing effect as a component or as the oleogel-forming agent of an oleogel. The wound healing effect of a triterpene-containing oleogel is, of course, not restricted to an oleogel having such a special triterpene composition. Three further triterpene compositions are specified as examples hereafter, which were used to manufacture oleogels, whose wound healing effect was verified on the basis of the "porcine ex-vivo wound model." The main components and the particular fraction in weight-percent are specified hereafter for these compositions, which are referred to as compositions Composition II:
betulin: 86.85 weight-percent
lupeol: 3.94 weight-percent
betulinic acid: 3.52 weight-percent
erythrodiol: 0.77 weight-percent
oleanolic acid: 0.62 weight-percent
Composition III:
betulin: 78.32 weight-percent
lupeol: 7.18 weight-percent
betulinic acid: 3.46 weight-percent
erythrodiol: 0.77 weight-percent
oleanolic acid: 0.63 weight-percent
Composition IV:
betulin: 60.50 weight-percent
lupeol: 25.43 weight-percent
betulinic acid: 1.68 weight-percent
erythrodiol: 1.47 weight-percent
oleanolic acid: 0.48 weight-percent As the example of composition III, which has a comparatively small betulin fraction, shows in particular, a high betulin fraction does not necessarily have to be provided for good wound healing.

The joint fraction of betulin and lupeol in compositions I-IV is greater than 80 weight-percent in each case, in particular greater than 85 weight-percent. The fraction in which the individual triterpenes are provided is dependent in particular on the plants or plant parts from which the triterpene-containing powder was obtained. However, good wound healing is not dependent on the special composition of the triterpene-containing powder. Rather, oleogels having arbitrary triterpenes as the oleogel-forming agents appear to have good wound healing properties.

In addition to sunflower oil, of course, arbitrary other fats or oils, which are non-toxic for humans or for mammals or which are medically applicable, are also suitable for manufacturing the oleogel.

What is claimed is:

1. A method for treating epidermolysis bullosa in a patient in need thereof, comprising topically administering to the patient an oleogel comprising a triterpene fraction, wherein the triterpene fraction comprises betulin.

2. The method of claim 1, wherein the method comprises topically administering the oleogel to an area of wounds caused by epidermolysis bullosa.

3. The method of claim 1, wherein the method comprises topically administering the oleogel to an area of epidermolysis bullosa comprising blisters.

4. The method of claim 1, wherein the triterpene fraction comprises between 1 weight-percent and 20 weight-percent of the oleogel.

5. The method of claim 4, wherein the triterpene fraction comprises between 6 weight-percent and 12 weight-percent of the oleogel.

6. The method of claim 1, wherein the fraction of betulin in the triterpene fraction is greater than 60 weight-percent.

7. The method of claim 1, wherein the fraction of betulin in the triterpene fraction is greater than 80 weight-percent.

8. The method of claim 1, wherein the triterpene fraction further comprises lupeol.

9. The method of claim 8, wherein the joint fraction of betulin and lupeol in the triterpene is greater than 80 weight-percent in the triterpene fraction.

10. The method of claim 8, wherein the joint fraction of betulin and lupeol is greater than 85 weight-percent in the triterpene fraction.

11. The method of claim 1, wherein the oleogel further comprises a nonpolar liquid.

12. The method of claim 11, wherein the nonpolar liquid is a plant, animal, mineral, or synthetic oil.

13. The method of claim 12, wherein the plant oil is a vegetable oil which is selected from one of the following: sunflower oil, olive oil, avocado oil, and almond oil.

14. The method of claim 11, wherein the nonpolar liquid consists of sunflower oil.

15. The method of claim 11, wherein the nonpolar liquid fraction comprises between 80 weight-percent and 99 weight-percent in relation to the total weight of the oleogel, and wherein the triterprene fraction comprises between 1 weight-percent and 20 weight-percent in relation to the total weight of the oleogel.

16. The method of claim 1, wherein the oleogel further comprises betulinic acid, oleanolic acid, and erythrodiol.

17. The method of claim 1, wherein the patient is a human.

18. The method of claim 1, wherein the epidermolysis bullosa is epidermolysis bullosa junctionalis, epidermolysis bullosa simplex, dystrophic epidermolysis bullosa, or epidermolysis bullosa dystrophica inversa.

* * * * *